United States Patent [19]
Miesel et al.

[11] Patent Number: 6,077,227
[45] Date of Patent: Jun. 20, 2000

[54] METHOD FOR MANUFACTURE AND IMPLANT OF AN IMPLANTABLE BLOOD VESSEL CUFF

[75] Inventors: Keith A. Miesel, St. Paul; Lee Stylos, Stillwater, both of Minn.

[73] Assignee: Medtronic, Inc., Minneapolis, Minn.

[21] Appl. No.: 09/221,547

[22] Filed: Dec. 28, 1998

[51] Int. Cl.[7] .............................. A61B 5/02; A61B 19/00
[52] U.S. Cl. .................. 600/486; 600/488; 600/300; 128/897; 128/898; 128/899; 623/1
[58] Field of Search ..................... 600/486, 485, 600/488, 504, 300; 623/1; 128/897, 898, 899

[56] References Cited

U.S. PATENT DOCUMENTS

| | | |
|---|---|---|
| 3,926,179 | 12/1975 | Petzke et al. . |
| 4,190,057 | 2/1980 | Hill et al. .............................. 600/486 |
| 4,227,407 | 10/1980 | Drost . |
| 4,256,094 | 3/1981 | Kapp et al. .............................. 600/486 |
| 4,269,193 | 5/1981 | Eckerle . |
| 4,346,604 | 8/1982 | Snook et al. . |
| 4,373,527 | 2/1983 | Fischell . |
| 4,600,855 | 7/1986 | Strachan .............................. 310/338 |
| 4,799,499 | 1/1989 | Bisping . |
| 4,802,488 | 2/1989 | Eckerle . |
| 4,803,987 | 2/1989 | Calfee et al. . |
| 4,924,872 | 5/1990 | Frank .............................. 600/486 |
| 5,005,574 | 4/1991 | Fearnot et al. . |
| 5,113,859 | 5/1992 | Funke . |
| 5,131,388 | 7/1992 | Pless et al. . |
| 5,144,949 | 9/1992 | Olson . |
| 5,188,106 | 2/1993 | Nappholz et al. . |
| 5,199,428 | 4/1993 | Obel et al. . |
| 5,318,596 | 6/1994 | Barreras et al. . |
| 5,409,009 | 4/1995 | Olson . |
| 5,411,031 | 5/1995 | Yomtov . |
| 5,545,186 | 8/1996 | Olson et al. . |
| 5,564,434 | 10/1996 | Halperin et al. . |
| 5,586,629 | 12/1996 | Shoberg et al. . |
| 5,596,986 | 1/1997 | Goldfarb . |
| 5,681,285 | 10/1997 | Ford et al. . |
| 5,687,734 | 11/1997 | Dempsey et al. . |
| 5,693,676 | 12/1997 | Gorfine . |
| 5,782,774 | 7/1998 | Shmulewitz . |
| 5,791,344 | 8/1998 | Schulman et al. . |
| 5,807,336 | 9/1998 | Russo et al. . |
| 5,873,837 | 2/1999 | Lieber et al. .............................. 600/504 |

*Primary Examiner*—Max Hindenburg
*Assistant Examiner*—Navin Natnithithadha
*Attorney, Agent, or Firm*—Harold R. Patton

[57] ABSTRACT

A method for construction ond delivery of a novel implantable medical device provides for use of a kit having sizeable fixture components for holding a blood vessel and a sensor portion connectable during surgery to the appropriately sized fixture.

17 Claims, 20 Drawing Sheets

SECTION A-A

SECTION B-B

METHOD FOR MANUFACTURE AND IMPLANT OF AN IMPLANTABLE BLOOD VESSEL CUFF

This invention relates to the field of implantable monitoring devices and is partially suitable for long term monitoring of physiologic parameters including most particularly blood pressure from small arteries.

BACKGROUND

Currently no device is available to automatically, continuously and chronically monitor blood pressure extravascularly. Sphygmomanometers are used to externally monitor blood pressure through the use of an external cuff. In common hospital parlance, stations having what are called inaccurately 'dynamap' systems (probably this misnomer is derived from the Johnson & Johnson "DINAMAP" (R) patient monitor systems, which use various blood pressure cuffs) automate these measures for discrete data point analysis. In either system type, the inflatable cuff or other pressure monitoring apparatae are bulky, impede blood flow and require operating personnel to make measurements. As a result these external systems are limited in usefulness to less than 24 hours in common usage. Numerous intravascular and paracorporeal automated pressure sensors have been developed to automate blood pressure monitoring of critically ill patients in hospital settings and for surgical patients. Typically these are composed of a moveable or dispensable membrane surface that by its associations with an electrical sensor produces a signal indicative of the pressure on the membrane. Not only is the usefulness of such devices limited to acute situations where access to the insides of a blood vessel is available, but the mechanical configurations are complex. Accordingly such devices are only able to provide blood pressure readings for a very limited period of time, and in circumstances of intense patient care, like in a hospital setting.

Using currently available internal to the circulatory system systems, at present time there is no good method for chronically measuring blood pressure on the left side of the circulatory system without actually placing a device in contact with the blood. This of course presents a site for thrombogenesis and the possibility of subsequent stroke. If no sensor is placed directly in contact with the blood the challenge is then sensing blood pressure through an arterial wall without introducing errors due to the structure of the arteries supporting all or part of the pressure load.

Further, there is no good present method for continuously sensing over a long period of weeks or months, even including devices which activate a mechanical occluder or cuff so as to provide data beyond mere systolic and diastolic values.

Perhaps the most advanced pressure sensor at the present time is described in some detail in U.S. Pat. No. 5,564,434, incorporated herein by this reference in its entirety. However, this blood pressure sensor is designed for dwelling in the heart of the patient on the heart's right side. Thus any thrombogensis created by the artificial material presence in the blood stream would have limited capacity to damage the patient that is, could not cause a stroke because any thromboses thrown by the device would end up in the patients lung. Thus this patent highlights the difficulty in achieving left side blood pressure measurements.

Other prior systems for attempting to meet some of the requirements described just above include U.S. Pat. No. 4,256,094 issued to Kapp et al, and incorporated herein by this reference in its entirety. This Kapp teaching requires a fairly complex mechanical system including a liquid pump and reservoir and programmable controller for cuffing or occluding the blood flow in the artery, difficulties which are obviated completely by the present invention.

External devices include those described in U.S. Pat. No. 3,926,179, and three which describe a watch mounted external device, U.S. Pat. Nos. 4,802,488; 4,799,49, and 4,269, 193 all four hereby incorporated herein by this reference in its entirety. Accordingly, there is a need for a device to enable the continuous chronic monitoring of patient blood pressure automatically and at low cost. To provide such a device without the requirement for vascular access and which could safely monitor the left side of the vascular system as well as the venous system would be of no small additional benefit. It is also an advantage to be able to provide additional devices for deploying sensors chronically to other vessels in the body for sensing other physiologic conditions(e.g. phlebitis).

Such devices as are described herein can be applied to monitoring patients with hypertension without cumbersome discrete point analysis over long terms with many hospital or clinic visits. Dosage accuracy can be enhanced with continuous long term monitoring of blood pressure for administration of hypertensive medications. It is also helpful for interventions to many disease processes such as diabetes, renal and neurologic disease, internal medicine and transplant patients, and any condition where surveillance of patient compliance could be helpful. Not only can continuous systolic, diastolic and pulse pressure monitoring be done with a minimally invasive implant, but additional or just different physiologic signals can be monitored, leaving wide open the scope of application of devices based on this invention.

Thus, the applicability of this invention is not limited to sensing blood pressure however. It should be recognized right from the start that the invention described herein can be used to obviate the use of many sensors which otherwise would require implantation into an active artery or vein system.

For example in U.S. Pat. No. 5,409 (also incorporated in its entirety by this reference) the blood flow is measured using permanently implantable lead within a vein adjacent to an artery. However, using our inventive fixture, flow, temperature, pressure, pulse rate, an even blood oximetry, as well as any other measurement that needs to be taken by a sensor next to the blood flowing through a artery or a vein can be accomplished using a device based on the inventive concepts described herein.

By providing accurate, continuous monitoring of patient blood pressure and other physiologic measures, a profile of patient status during activities of daily living and over prolonged intervals can accurately depict the patient's true hemodynamic health status over months of use. Such automatic monitoring circumvents patient compliance and operator compliance issues which are problematic in the use of external devices. Particularly, the fixture with sensors concepts described herein can be applied to peripheral, internal and neurologic blood and other fluid pressures, flow and so forth. Carotid arterial blood pressure, pulmonary venous blood pressure and cerebral ventricular pressure associated with hydrocephalous are just three examples. The device could be used to monitor the formation of transudate and exhudate fluids, such as in conditions of subcutaneous edema. The device can of course be useful as a research tool, and may find many uses in veterinary medicine and monitoring.

SUMMARY OF THE INVENTION

Figure 1:
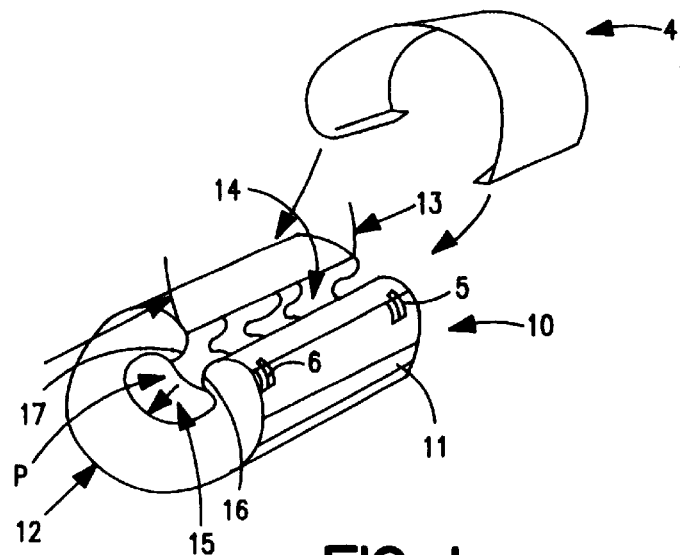
FIG. 1 is a perspective view of a preferred embodiment.

A number of general and specific objectives are set forth for what this invention can provide, and also a number of general and specific features. All of these features and objectives can be met individually or in combination by the description which follows.

In one preferred embodiment the sensor system consists of a side-sensing chronically-implantable absolute pressure sensor incorporated into the inventive structure. This sensor may be similar or identical to the one described in U.S. Pat. No. 5,564,434. To avoid unneeded prolixity, the just above mentioned and all subsequently mentioned patents are incorporated herein in their entireties by this reference sentence, and this sentence is operative to so incorporate all such mentioned patents at each such mention without the need of repeated recitation of this statement or its equivalent at the location of such mention.

The pressure sensor is packaged inside or in close and operative association with a clamp type structure which we often refer to as a fixture which holds an artery against the sensor diaphragm or against the pressure transferring medium (such as silicone or medical grade adhesive) capable of accurately transferring or transporting pressure from the artery side wall to the sensor diaphragm. The shape of the artery channel through the fixture's clamp-like structure is such that it slightly deforms the artery to provide a flattening of the artery (in cross section) in the region where it passes over the sensor diaphragm or the silicone adhesive between the sensor diaphragm and the artery. This flattening of the artery causes pressure interior to the artery to be supported by the sensor structure rather than the artery wall structure. This causes the arterial pressure to be passed through the artery wall to be detected by the pressure sensor.

This effect can be enhanced by varying the shape of the tunnel or channel through which the vessel is placed as described in some detail below.

Calibration can be effected if required once the device is in place which may account for variations in wall thickness or other features of the vessels or for other reasons known in the pressure sensor art. Another feature of the clamp structure is on the opposite side (in this preferred embodiment) from the pressure diaphragm. What can be described as a slit is provided along the length of the clamp structure, this slit being substantially narrower than the diameter of the artery. The artery is inserted into the clamp by squeezing the artery (or clamping it off upstream) and passing it's collapsed form through the slit and than releasing the artery and allowing it to spring out to conform to the shape of the insides of the clamp's channel. The pressure inside the artery will tend to keep the artery confined within the clamp channel without the need of any additional fastening hardware, thus reducing the likelihood of complications.

The artery can further be secured within the fixture (which we sometimes call an artery cuff) by forming the access slit in a serpentine shape, that is having a curved cut through which the filled vessel cannot easily slip out, once it has become secured within the fixture.

Thus, this invention allows for the measuring for pressure within a artery or other vessel (like a vein) through a vessel wall by causing a flattening of the vessel at the point of sensing. It teaches the method of inserting and retaining a vessel within the clamp's structure to hold the vessel against the pressure sensor. It provides a second pressure sensor on the backside of the arterial pressure sensor this second sensor not being in contact of the vessel which can be used to measure ambient pressure for calculation of "gage" pressure. This invention provides for chronic measurement for arterial pressure through the arterial wall without needing to contact the inside of the blood vessel.

In other preferred embodiments, other sensors for sensing other physiologic parameters could either supplement the pressure sensor or replace it as described elsewhere in more detail. For examples, temperature could be sensed and used for various purposes such as was described for rate control in pacing in U.S. Pat. Nos. 5,005,574 or 4,803,987 (incorporated herein by this reference), or temperature could be used as just another physiologic sense to monitor for therapeutic, research, drug titration and other medical purposes. Other sensors could provide additional data for similar medical uses like optical sensors for oximetry or pulse oximetry and even partial pressure of oxygen can be measured and stored or used for various purposes. An example of a sensor that could be used for this is described in a patent incorporated herein by reference; U.S. Pat. No. 5,596,986 (Blood Oximeter). Other sensors could be substituted or used in conjunction with the pressure sensor to provide other physiologic data for use in monitoring and treating patients. Merely supplying electrode surfaces in the fixture would provide the structure to make impedance measurements could be used for local flow characteristics, or piezocrystals and similar transducers for ultrasound generation could also or alternatively measure flow or viscosity of the fluid in the vessel held in the fixture in accord with this invention.

Many improvements in monitoring a patient's health can come about through the use of the inventive fixture described herein. Methods of construction and use are also described. Meeting any one of these described goals or objectives or any combination or all of them is the purpose of this invention.

DETAILED DESCRIPTION OF THE PREFERRED EMBODIMENTS

Referring first to FIG. 1, a device 10 illustrates a preferred embodiment of the invention. The device 10 is constructed of an outer shell 11 continuous with the inner surface 15. It is essentially a tubular shape having a slit 14 therein extending along the length. The length is indicated by arrows 13 and the slit opening has two opposing surfaces 16 and 17 which are narrow relative to a deeper passage P which forms the main portion of the tunnel through the device 10 beneath the slit 14. In most preferred embodiments the sensors will be housed within the area between the passage P and the outer surface 11 indicated here by arrows 12. The surface 15 will be modified to accept the active end of any sensors employed, for operational effectiveness. Alternatively other areas of the surface of the tunnel passage P's walls may be used.

The device may be built of metal or plastic which is tolerated for long term implantation into a living body. Implantable medical devices are commonly constructed of titanium currently; and ceramic, plastic, and silicone are among other commonly used materials for implanted medical devices. Any biocompatitable material maybe used. Our first embodiments tested were constructed of titanium.

Figure 2:
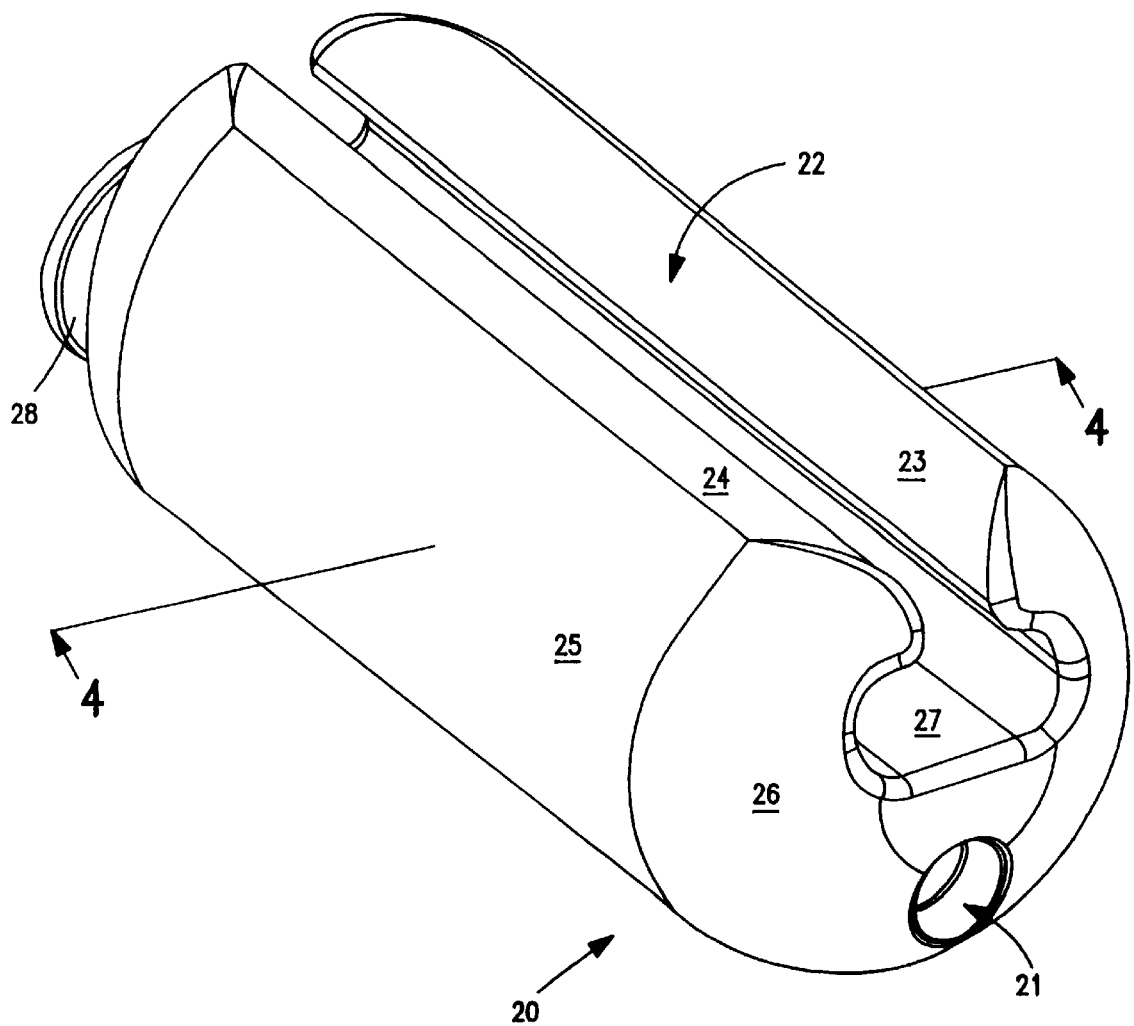
FIG. 2 is a perspective of another preferred embodiment of the invention.

FIG. 2 illustrates another preferred embodiment of the invention. The device 20 has a passage there through, extending from the sides with openings 21 to area 28 in which the pressure sensor may be inserted and is preferably located. The pressure sensor is not visible from this view. The device 20 has a slit 22 with two opposing surfaces 23 and 24. These are rounded into the external shape of the device 20 and continuous with the external surface 25 and 26 as well as with the substantially flat internal surface 27.

Figure 3:
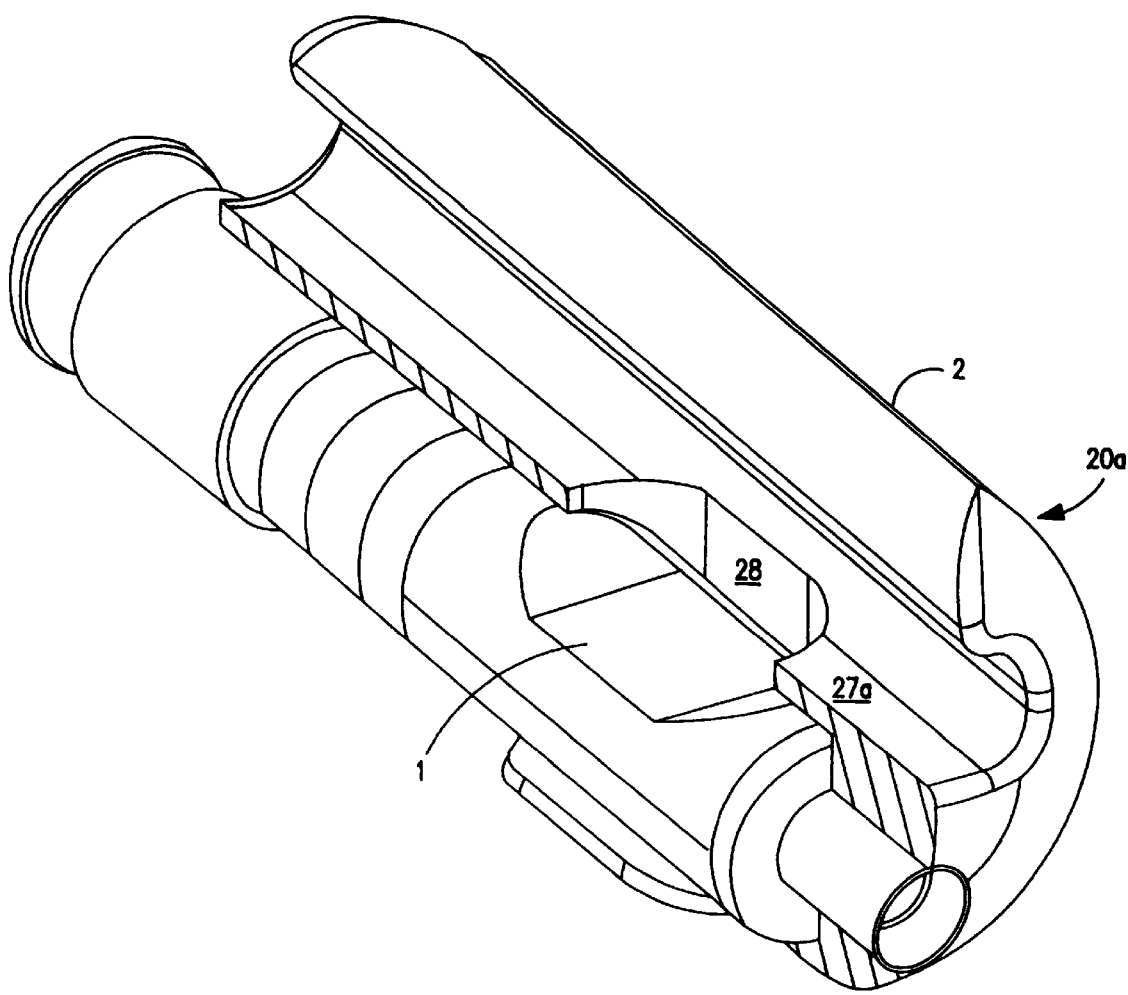
FIG. 3 is a cut away view of FIG. 2.

Referring now to FIG. 3, the internal details of the device can be better seen. The active diaphragm surface 1 is in this embodiment the functional equivalent or similar to the diaphragm 54 of the U.S. Pat. No. 5,564,434 patent referred to above. Any deflection of this diaphragm 1 will register a change in pressure by the pressure sensor. As with any sensor, this will produce a signal that has a value which can be stored, telemetered out, or used directly to affect the operation of an implantable medical device. The same is true with all the sensors in all the embodiments.

The aperture defined by wall 28 extends up to the surface 27a of device 20a. This aperture will be filled in by medical adhesive in the preferred embodiment to transmit pressure directly from the blood vessel, (an arteriole in the preferred embodiment). The blood vessel will be captured within the clamping structure 20a lying along surface 27a.

It is acceptable to build the inventive device such that the diaphragm (in the case of the pressure sensor, or other active surface of any other sensor) forms a surface area coextensive with surface 27a for direct contact with the vessel especially for embodiments using sensors requiring closer contact to the vessel such construction is advisable.

Figure 4:
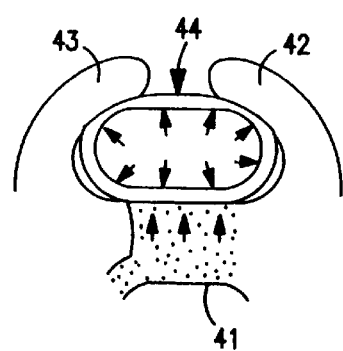
FIG. 4 is a cut away view of the upper portion of the embodiment illustrated in FIG. 2 taken at line 4—4 of FIG. 2.
Figure 5:
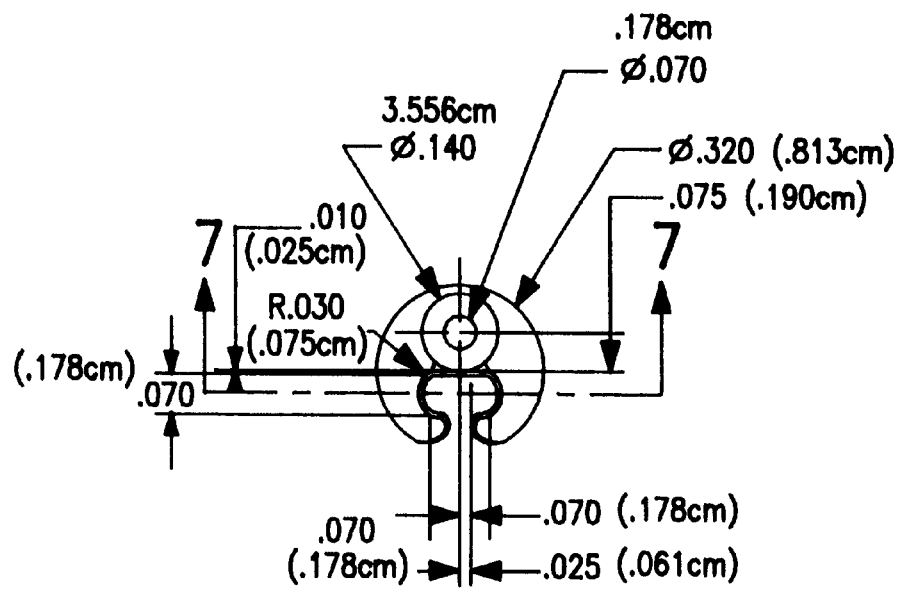
FIG. 5 is a frontal view of the embodiment described with respect to FIG. 2.
Figure 6:
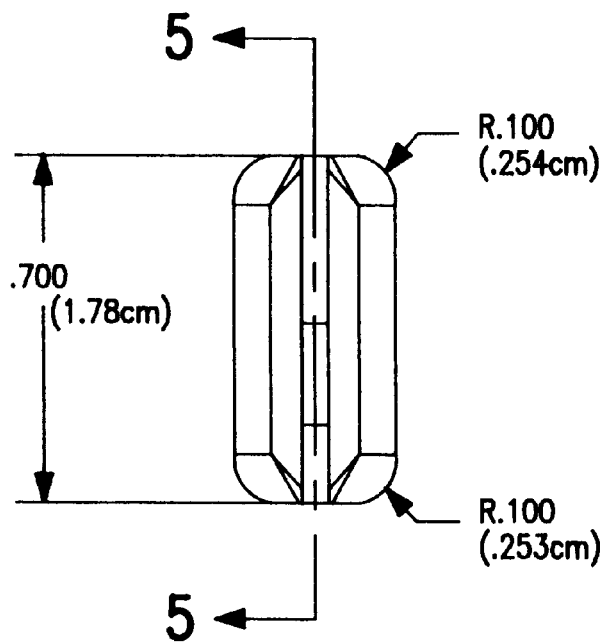
FIG. 6 is a top view of the device of FIG. 2.
Figure 7:
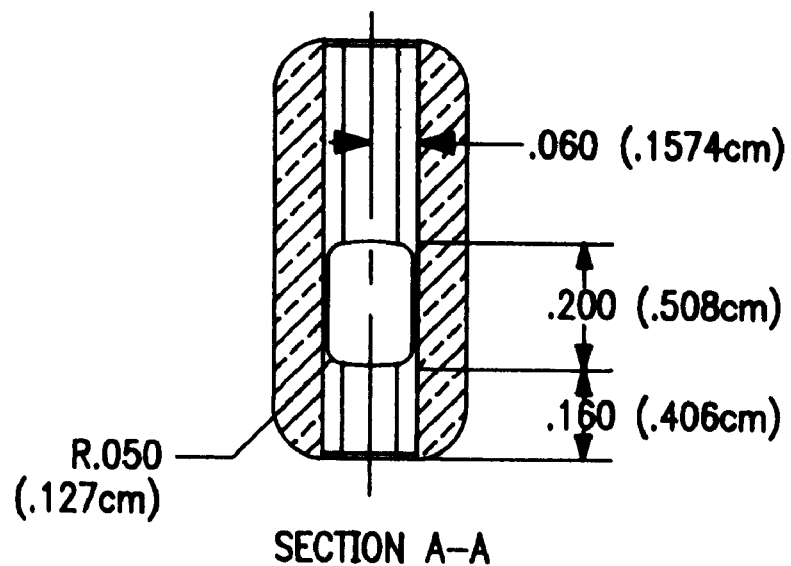
FIG. 7 is a sectional view taken at line AA of FIG. 5.
Figure 8:
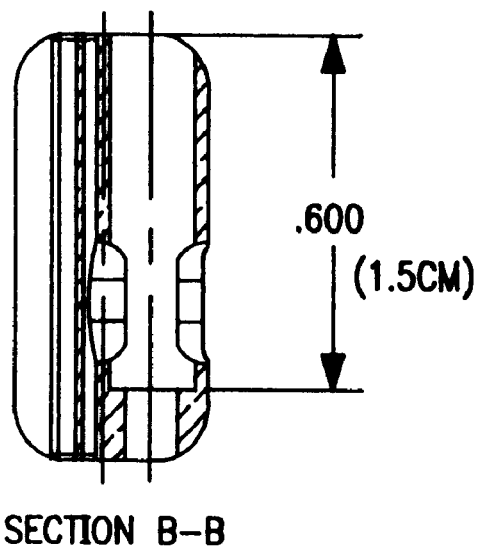
FIG. 8 is a sectional of FIG. 6 taken at line BB.

The construction of the FIG. 3 device may be illustrated more simply with reference to the cross section in FIG. 4 in which the sensor structure 41 is shown attached to the medical adhesive or pressure transfer medium Ps, through which the arterial pressure Pa, will transmitted through the flattened arterial wall lying against the pressure transmission medium. Thus, the arms 42 and 43 provide the clamping structure that holds the artery in place for the sensor measurement to be made. In the alternative, embodiments employing for example oxygen sensors based on light transmittance, reflectance or absorption, these arms 42 may be covered with light reflective surfaces, or alternatively may also contain sensors instead of or in addition to the surface 27a. Note that in some embodiments the artery or other vessel wall 44 may bulge into the gap between arms 42 and 43.

The absolute size of the implanted sensor device can be adjusted to any specification so as to fit around the particular arterial, artery, vein, venuole, or other vessel through the wall of which one desires to make physiological measurements. In FIGS. 5–10, numerals indicate the size in centimeters of a preferred embodiment fixture similar to that shown in cross section in FIG. 3.

Figure 9:
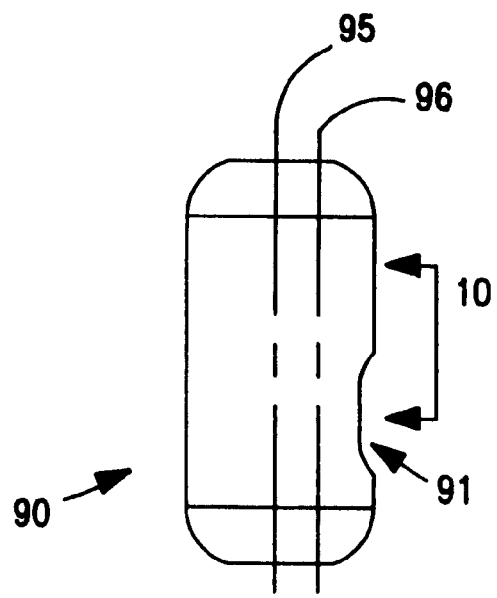
FIG. 9 is a side view of one embodiment of the sensor fixture in accord with the invention.
Figure 10:
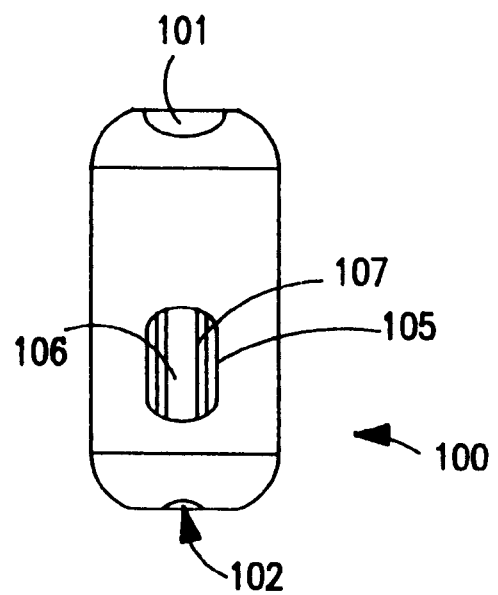
FIG. 10. is a back view of the fixture of FIG. 4.

In FIG. 9, The inventive fixture 90 is shown in side view. The line 95 indicates the location of the flat surface and the line 96 indicates the location of the base of the slit or opposite to the flat surface. Taken together they define one diameter of the tunnel passageway that runs through the fixture and in which the vessel should rest when in use. A depression 91 is seen from this view. This depression is formed in the titanium block from which the fixture is formed in order to make the opening between the pressure sensor diaphragm on the surface coextensive with line 95. In FIG. 10, the outer edge of the generally flat, sensor bearing surface of the clamp's passageway can be seen at 107. The space 106 is the slit through the opposite side of said passageway. Openings 102 and 101 are the stop and entry ends for the pressure sensor which will be inserted into the fixture 100 to make the completed device.

Figure 11A:
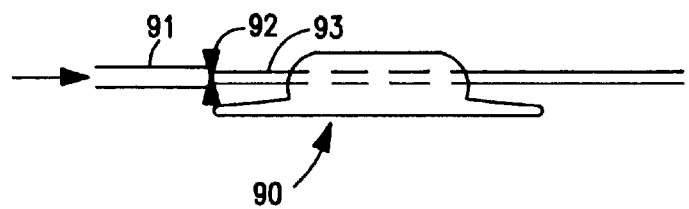
FIG. 11a is a side view of another embodiment of the invention surrounding an arteriole artery or other blood vessel which is pinched off to fit into an inventive fixture in accord with a preferred embodiment.
Figure 11B:
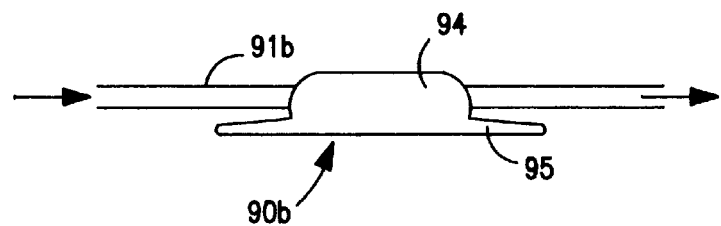
FIG. 11b is another side view of the fixture and blood vessel of FIG. 11 with the normal flow restored.

FIG. 11a and 11b, illustrate the preferred method for having a body vessel (preferably a blood vessel) become surrounded and held by the clamp device, that is, the fixture, of this invention. In FIG. 11a, a clamp 92 can be used to prevent the continuing flow of blood through a vessel 91 thereby producing a collapsed vessel 93. This collapsed vessel can easily be slid through the slit at the top of device 90 so that it rests within the passageway as shown. Once the clamp 92 is removed (see FIG. 11b). The blood can flow through the vessel 91b thus clamping the vessel into the passageway in the clamp part 94 of device 90b. Additional physical features may be connected to the clamp device such as wings 95 or suture holes (not shown) which could be sewed onto tissue within the body to further stabilize the device, although when used with arterial vessels we have found no need for such further stabilization.

If desired, a clip, preferably of a deformable springy material like spring steel or other metal or plastic, may be fit over the top of the slit to help ensure that the vessel cannot escape the clamp. Such a clip is illustrated on FIG. 1 as clip 4, having flat stabilizing ends to keep it from rotating around the fixture 10, and the fixture 10 should have bumps or ridges 5 and 6 to keep the clip from sliding, or some other detent and ridge or other mechanical arrangement could be used to ensure the clip 4 does not slide once in place.

Figure 12:
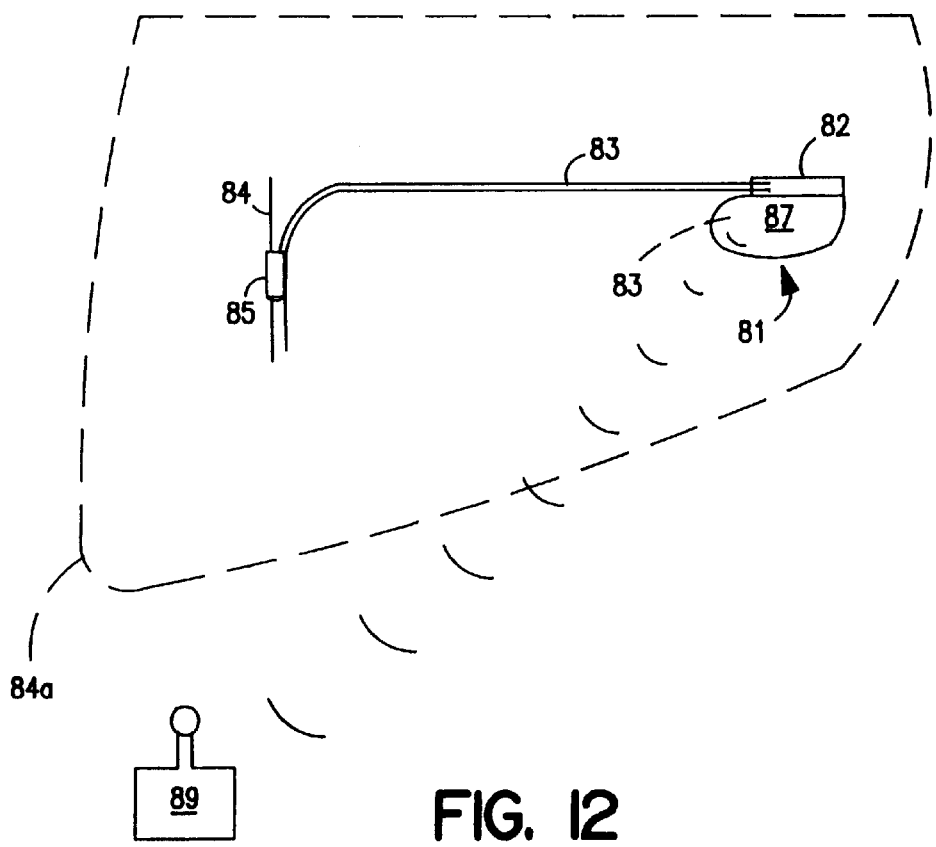
FIG. 12 is an illustration of am implantable medical device for monitoring data produced by the inventive fixture connected to it by a lead.

Refer now to FIG. 12, an implantable medical device 81 is illustrated having a body 87 containing a power source and appropriate electronics for powering and reading out data from the sensors in the device 85. It may also contain communications circuits for receiving signals from the inventive fixture and sensor device and/or from other devices in a living body, and for communication with devices external to the body as well. It may likewise contain the operative features and structures to be a drug pump, a cardiac pacemaker, a cardiodefibrillator, a nerve stimulator or just an implantable monitor, or any combination of these.

Device 85 is connected to the inventive structure by a lead 83 in the preferred embodiment. This lead may be similar in construction to leads currently used in pacemakers and cardio defibrillators and the like in that they contain a conductor for bringing electric power to and from the sensor device in the clamp 85. Here a vessel 84 is illustrated running through the clamp device 85 The device may contain its own power supply circuitry, communications circuitry and so forth as desired. Presently it is most preferred that only the sensor(s) and some electronics associated with processing the transducer signals for such sensor (s) be contained in a sensor capsule of the inventive device.

Figure 13:
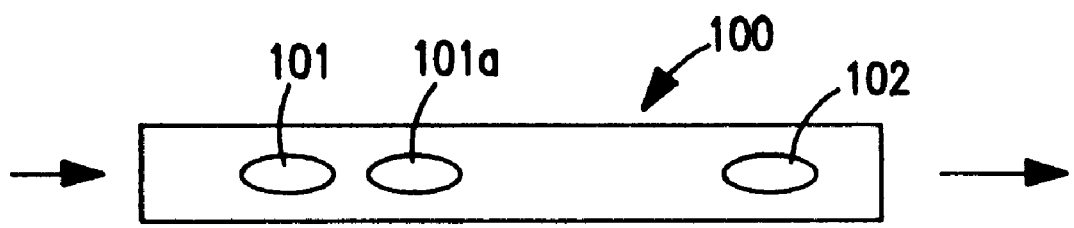
FIG. 13 is a view facing an inner sensor laden surface of the tunnel or passageway space for containing a living body's blood vessel as it may be constructed in accord with a preferred embodiment of the invention.

In FIG. 13, the lower surface of the passage 100 is shown separated from the device. The direction of blood flow is indicted by the arrows. In this setup two sensor areas 101 and 102 are provided to allow for differential readings upstream and down stream. In one preferred embodiment, a heater (preferably a resistive heater) would be included at area 101 or 101a or both, and a measurement of the temperature of the blood can then be taken at location 101 and 102 or at least at 102 and a determination made from these measurements relating to the viscosity of the blood itself or the speed of passage through the distance through the passage way between 101 or 101a and 102. This can be done using principles defined in U.S. Pat. No. 5,486,107 to Bonne et al hereby incorporated in its entirety by this reference hereto, which describes the use of specific heat and thermal conductivity to determine characteristics of a gas flowing past a sensor array.

Alternatively, Doppler sensors or ultrasound transducers may be used as were used in U.S. Pat. No. 5,409,009 patent cited above and incorporated herein by reference for determining flow or other physiologic parameters, using this or similar sensor array patterns or even located at a single point as is the pressure transducer of the first disclosed embodiment. An example is found in U.S. Pat. No. 4,227,407 (incorporated herein in its entirety by this reference) detailing how the transducers should be located relative to the conduit, here the contained blood vessel, to generate an electric signal proportional to fluid flow.

Figure 14:
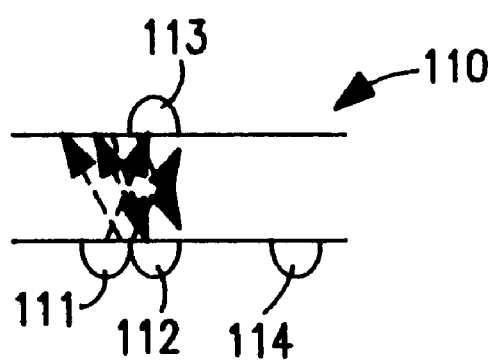
FIG. 14 illustrates a sensor array having an emitting element, a receiving element and their position within the inventive fixture relative to a blood vessel.

In FIG. 14, the internal passageway 110 of an inventive clamp device, may have an infra red sending and receiving array 111 and 112 mounted into the wall thereof so that the light L can penetrate the vascular wall VW and provide measurements for indications for the percentage of oxygen's satiation of the blood passing through the passageway 110.

Alternatively, these sensor locations can be adjusted to be on opposite sides of the fixture and the vessel, for example at points 113 and 114. Further, such configurations can be useful for impedance sensing to measure flow rate, viscosity and the like or for employing Doppler transducers for similar measurements. An example of placement of impedance electrodes relative to a flow duct (in this reference the Aorta), is found in U.S. Pat. No. 5,782,774, also incorporated by reference. Clearly to measure cardiac output over a period of days or months or even years by incorporating the electrode configuration around a less vital blood vessel downstream from the Aorta would provide significant benefit to medical science, and to the management of the health of a patient using our device.

Electromagnetic measurements can be made with electrode placement as indicated in U.S. Pat. No. 4,346,604 also, if desired, and the magnetic positioning can be adjusted to be a part of the fixture device itself.

Of course it must be recognized that a feedback loop can be created using the measurements taken by sensors in the clamp device to deliver therapy to a living body into which the clamp device has been implanted. Thus, a fast acting blood pressure medication maybe monitored on a moment by moment basis throughout a patients daily activities by the use of such a clamp device associated with measurement circuitry and possibly processing circuitry and memory circuits implanted therewith. Data from the fixture device sensors can be used to modify programs for generating electrical pulses to stimulate nerves and to adjust pacing rate by coordination with an implantable pulse generator that has leads directing electrical energy to the appropriate bodily tissue.

This kind of closed loop feedback mechanism has long been established a potential use for implanted medical devices. In one example, in U.S. Pat. No. 5,199,428, Obel et al., incorporated by this reference, showed that a measure of ischemia could drive a cardiac pacemaker therapy and a vagal stimulator. Any of the physiologic signals measured by this device could provide the kind of input a closed loop control system would need for adjusting therapy, whether drug based via a drug pump, or stimulator based as in the rate delivered by a pacemaker or the frequency etc., delivered by a neurostimulator. Likewise, the signal data could be easily stored into historical memory in a device like that of 87 in FIG. 12, which has appropriate processing power and memory. Such a device can clearly have a telemetry circuit 88 which could transmit signals to an external device 89 which could communicate the signals to a hospital over phone lines or through wireless telemetry so that the doctor can manage his patients, be aware of changing conditions and even be alarmed about changes in patient condition without ever scheduling a visit. Examples of useful monitors include U.S. Pat. Nos. 5,807,336, 5,791,344, and 5,411,031.

Figure 15A:
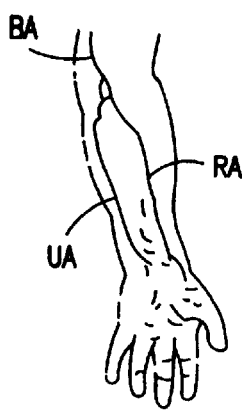
FIGS. 15a–e are illustrations of arterial blood vessel locations suitable fore use with one preferred embodiment of the invention.
Figure 15B:
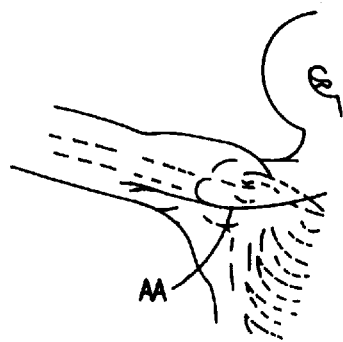
Figure 15C:
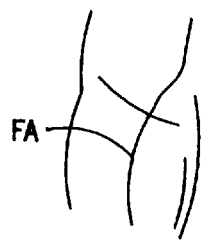
Figure 15D:
Figure 15E:
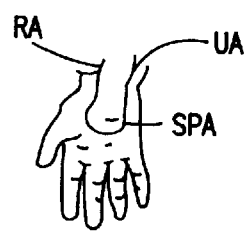

It may be preferred to implant the invention's fixture into locations illustrated in FIGS. 15a–e. FIG. 15a illustrates an arm having three highlighted locations for preferable mounting of the inventive blood pressure fixture in accord with this invention. The Axilary Artery provides another apt location in FIG. 15b. the Inguinal, and Femoral arteries as well as the posterior Tibial artery in FIGS. 15c and d, respectively provide additional useful locations as do the Radial Ulnar and Superficial Palmar arteries shown in FIG. 15e. Each of these locations provides particularly useful information and a combination of locations can be used so as to provide for a systemic or overall reading or to indicate that there is an imbalance in a given area or across the system.

Long term monitoring of any such arrangement of sensors or sensor structures can provide detailed measurement data that can be used for historical charting of the patient's conditions and long term patient management.

In FIG. 16, a perspective view of a fixture 130A has a cable 136 linking a pressure sensor, (not visible here) connected at a linking junction 137 to the fixture 130A. It is recognized that not all vessels to which the fixture will be used to surround will be of the same size and consequently, the inventive device will be made available in multiple sizes. The surgeon will select the appropriate sized fixture for the vessel and snap the pressure sensor into the one selected, either before or after the blood vessel is surrounded by the passageway in the fixture. The fixtures can be constructed of hylon or similar suitable biocompatible plastic, such as may be used in connector blocks for pacemakers or other implantable medical devices with electrical leads currently, or of ceramics or metals that may be acceptable.

A block of medical adhesive will have been formed in the well 134 prior to the surgeon connecting the pressure sensor into the fixture 130A. For construction purposes, if using a metallic, such as titanium block from which the device will be machined, the opening at 133 is what is left after wire electric discharge machining. It may be filled as desired in the completed device when prepared for use. To construct the entire device then, one would machine in the curves, the slit and the tunnel, then either the through hole at 133 or the space shown at 133a in FIGS. 16B and C to create the diaphragm. Then the assembly of the pressure capsule would be completed by bonding the sensor and electronics board to the lower surface of hole 133a so that the diaphragm contacts the sensor appropriately, and then sealing the sensor capsule. Next the through hole 133 can be filled with transmissive material up to surface 135 and the device connected to a lead if appropriate. Then the device can be sterilized and will be ready for use.

Figure 16A:
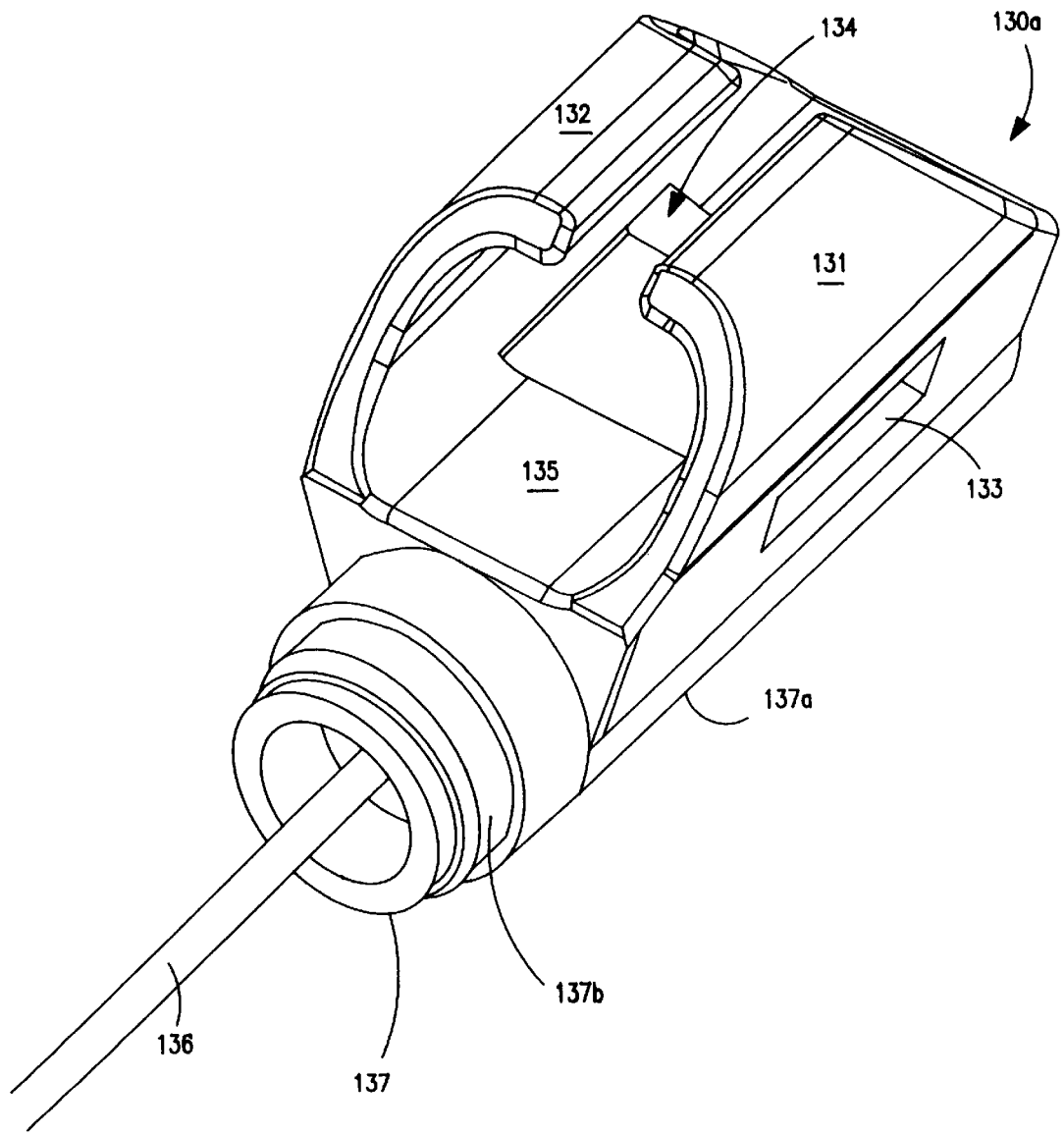
FIG. 16A is a perspective view of a preferred embodiment fixture configuration and connection to a lead.
Figure 16B:
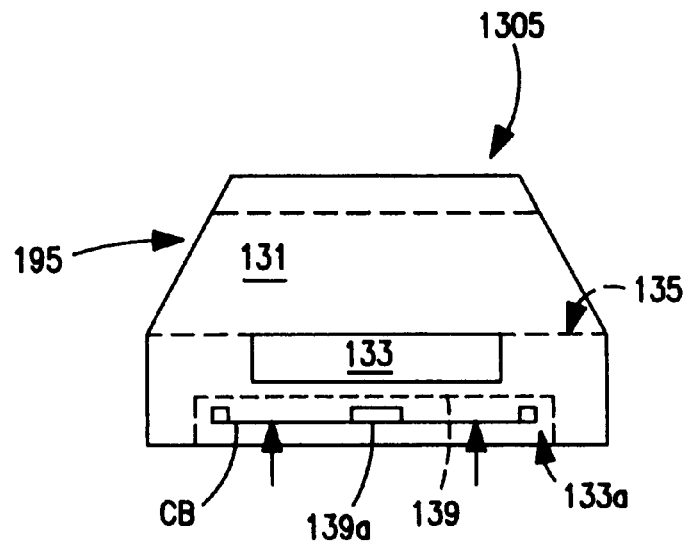
FIG. 16B is a side view of the top portion of the device illustrated in FIG. 16A.
Figure 16C:
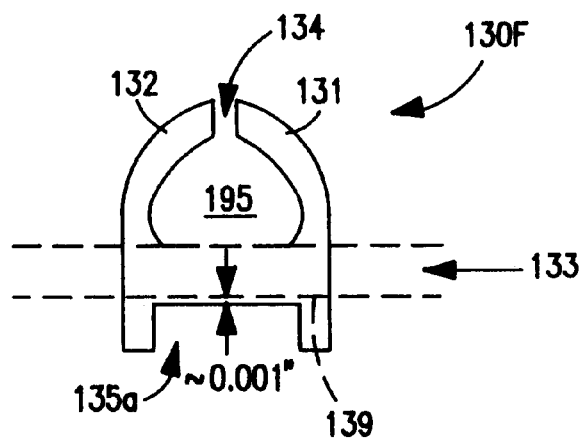
FIG. 16C is a facing view of the top portion of the device of FIG. 16A.

Details in the construction of the device of FIG. 16A can be more clearly seen with reference to FIGS. 16B and 16C. In FIG. 16B. The structure 130s is the same as the top portion of the device 137a. In one preferred embodiment of a titanium block that has been electric discharged machined to produce the outer configuration shown in these FIGS. 16A–C, including the tunnel like passage way 195 having the base 135 and a slit 134 at the top. To form this construction, the electric discharge machining first produces the slopped sides (if desired for the final design,) and then produces the tunnel like through passage way 195 and the slit 134. The rectangular passageway 133 must be machined very carefully because this step produces the pressure diaphragm itself. The lower surface of the pressure diaphragm which will be inside the pressure capsule is illustrated at line 139 in both FIGS. 16B and 16C. A circuit board CB containing the sensor package 139a will be inserted in the area 133a machined from the area of the block opposite the slit 134. For our purposes, the preferred thickness of the diaphragm formed by the lower surface of the hole provided at 133 and the upper surface provided in area 133a should be on the order of approximately 0.001 inches.

Figure 18:
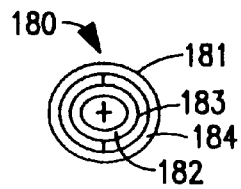
FIG. 18 is a cross sectional view of a cable or lead in accord with a preferred embodiment of the invention.

The cable 136 may be preferably manufactured with two conductors as illustrated in cross section 180 in FIG. 18, with one center wire 181 surrounded by a cabled or wound wire 183 spaced apart from each other by silicone or medical adhesive or other biocompatible and preferably non-conductive material in layer 182. Preferably also a sheath layer 184 surrounds the outer conductor. A current pacing lead construction with two coiled metal conductors would suffice as well, and many variations are possible, including merely twisted pair wires, straight conductors and the like. A coaxial configuration is preferred only because a less noisy signal will be obtained with such a structure. As fiber-optic communications channels and their uses with sensors become better able to handle the stresses of implant by technological innovation, such cables may also be employed, and perhaps preferred.

Figure 17:
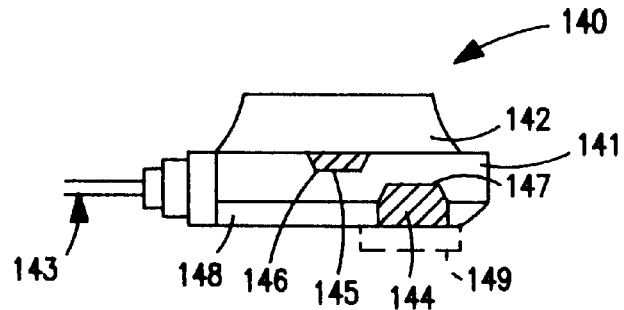
FIG. 17 is a side view of a preferred embodiment similar to that of FIG. 16A.

Referring now to FIG. 17, a side view of a structure like that of FIG. 16 is shown in cross section 140. The connecting cable 143 provides signal and power to what in the preferred embodiment is a titanium capsule 141 having two sensors at deformable membranes or plates 146 and 147, one at 147 being useful as a reference sensor. (If a reference sensor is used for any sensor, common mode noise can easily be canceled as is known in most sensor art fields. In the pressure field, by having an absolute measure of pressure available at a reference sensor protected from the environment of the measuring sensor, a value close to gage pressure can be obtained, as well as the differential represented by the value of the blood pressure signal. Accordingly, with such an embodiment we can cancel the effects of atmospheric pressure fluctuation as would be done in this art. So here, the sensor under plate 146 would sense the blood affected pressure through a window of preferably something that will transmit a regular approximation of the blood pressure in the vessel above it, such as cured medical adhesive, and the ambient or atmospheric pressure will be sensed above the plate 147, which faces an area of stable body tissue or is blocked off from it. Alternatively, a pressure sensor could be mounted within a capsule implanted in a more stable area of the body for use as the reference sensor.)

The sensor capsule 141 is fixedly mounted or formed into the fixture surrounding it which from this cross section is seen to be mainly comprised of the passageway supporting section 142 through which the vessel will be mounted when in operation and the retaining portion 148. To show one form of isolation structure for the reference sensor, a dotted section is shown at 149 which could be formed of the same hard plastic that preferably forms sections 148 and 147, which if perforated to allow fluid access to the window 144 will provide a good environment for reference pressure measurements. On FIG. 21, the outline of such a reference sensor is illustrated at 227, and the perforations at 228.

Figure 19:
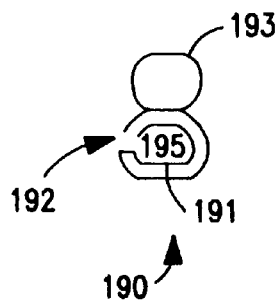
FIG. 19 is a cross sectional view of an alternative embodiment of the inventive fixture.

An alternative embodiment 190 is viewed cut across the tunnel shaped passageway 195 into which the vessel would be mounted in FIG. 19. In this embodiment the slit or opening 192 is near the flat internal surface 191, which indicates that the inventors considered the relative location to be non-critical. That is, it is not believed that the opening and the flat surface must be on opposite sides to perform sufficiently well to function. In fact, if one does not use a pressure sensor, it may not be necessary to flatten one side or even a part of one side of the inner surface of the tunnel like passageway. Also illustrated in FIG. 19, is the potential for maintaining all electronics, power sources telemetry, memory and other processing circuitry in direct contact with the sleeve or tunnel like passageway which will surround the vessel. In FIG. 19, this is shown with an adjoining housing area 193, which can be of any convenient shape. It is expected that in most preferred uses, the smallness of the sensor fixture will be of paramount importance, so such circuitry will at least for the near future be mounted in a housing separated by a conductor containing lead from the fixture. For some applications a fiber-optic cable may be preferred or may supplement the electrical conductors.

For example, a sensor fixture could be mounted around the radial artery or vein with a pressure sensor mounted in the fixture, and a conductor bearing lead tunneled through the arm to an implantable pulse generator in the patient's chest. This sensor would provide feedback regarding changes in the pressure within the patient's body at the extremity and this measurement set could be used to modify stimulation pulses sent by the pulse generator mounted in the chest t, for example, by sending pulses of greater intensity or duration to the carotid sinus through another electrical medical lead connected to stimulate at that location. As mentioned earlier, data in the sensor measurements provided by sensors mounted in the fixture can provide the basis for adaptive closed loop programs that provide changes in heart pacing stimulation or drug delivery from implanted drug pumps.

Additionally, the fixtures could be mounted to any body vessel including but not limited to bile ducts, pancreatic ducts, seminal vesicles, lymph vessels or any of the tubes involved in the Kidney function or the excretion of urine downstream therefrom, in short, on any vessel through which a fluid may flow, so as to take measurements of that fluid. The squeezing off of the body vessel provides for a smaller outer diameter that can fit through the opening or slit in the fixture, and then the vessel upon release will fill or overfill the internal diameter of the tunnel shaped passageway becoming thereby fixed thereto so that repeatable reliable long term measurements can be taken by a sensor structure mounted into the internal surface.

Figure 20:
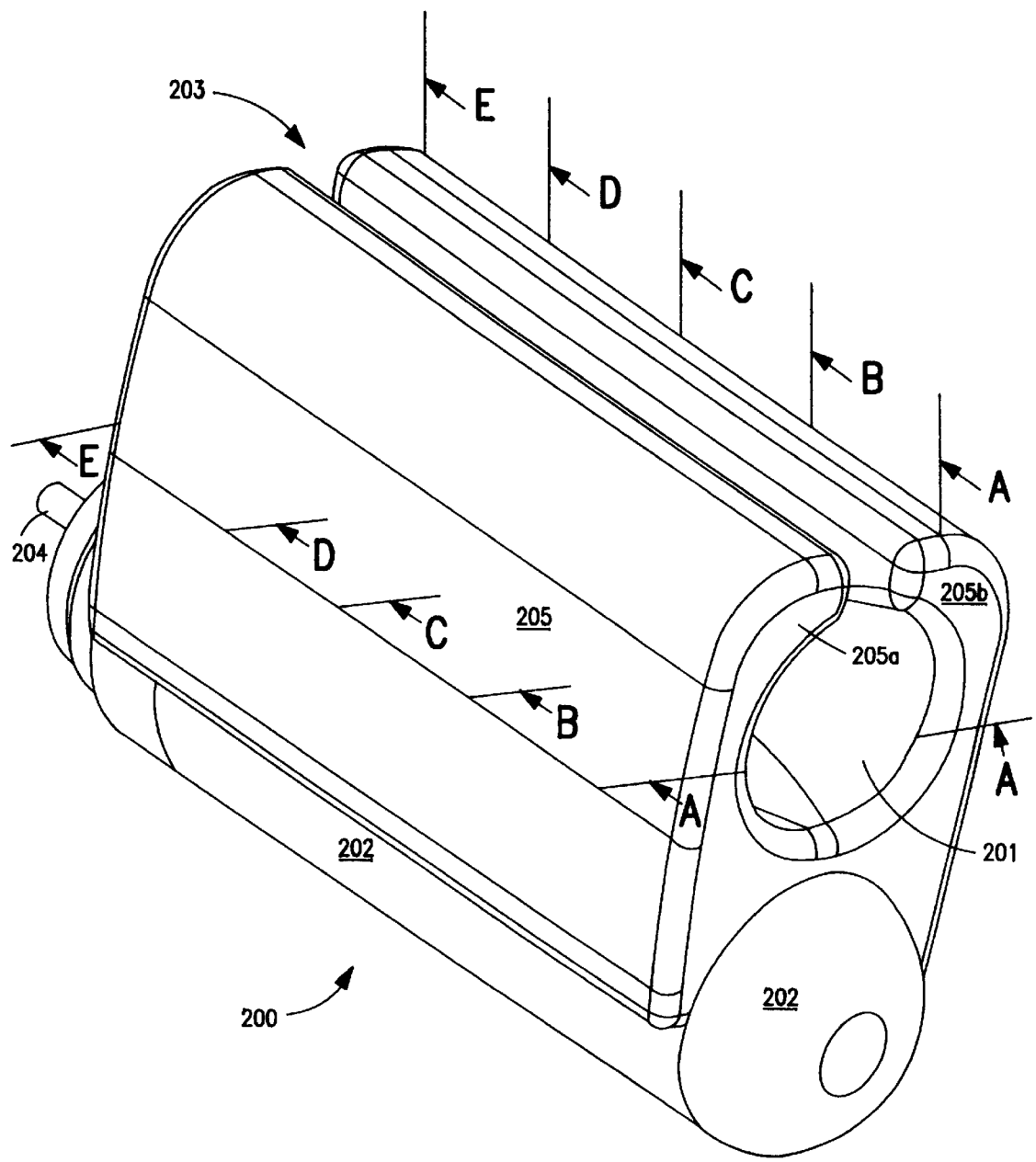
FIG. 20 is a perspective view of another preferred embodiment of the invention.
Figure 20A:
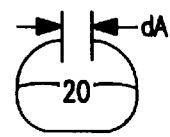
FIGS. 20A–E are cross sectional slices of the interior surface of the internal space, tunnel, or passageway for containing blood vessels in accord with a preferred embodiment of the invention. each is taken from section lines A–E as illustrated on FIG. 20.
Figure 20B:
Figure 20C:
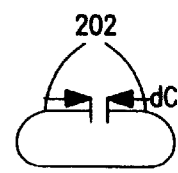
Figure 20D:
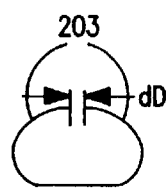
Figure 20E:
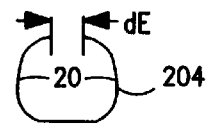

Referring now FIG. 20 in which an alternate preferred embodiment 200 is illustrated, a thin lead 204 can be connected to an end of the pressures sensor capsule 202 if desired. This lead 204 may be much thinner than a cardiac pacing lead (for example) since no coiling would be required for a conductor in such a lead. Optical communication could of course take place over an optical fiber (in lead 204) if the circumstances of the device suggests such a design would be preferred. In fact, use of not connected telemetric pathways for communications with the implantable device are an option and such communications with implantable medical devices has been known for some time.

The fixture for holding the blood vessel 205 again is shown to contain a tunnel or passageway 201 having a slit 203 along one side of it between the arms 205*a* and 205*b* of the fixtures body 205.

For convenience, the internal diameter of the tunnel space 201 is taken in views of the sections A–E, illustrated in an abbreviated form in FIGS. 20A–20E. Referring to these FIGS. 20A–E, it can be seen that the slit width dA–dE does not vary substantially in this preferred embodiment, even though the internal configuration of the tunnel does. Each of the internal diameters taken from the view lines A–E of FIG. 20 can be described as two rough semi circles, concave sides facing but spaced apart the length of a relatively flat line on the bottom which joins the semi circles 210–214, this flat area, in the preferred embodiments, being a cross sectional of the preferred substantially flat area in which the sensor(s) are most efficaciously placed. (Some variation from flatness and placement are within the scope of the concepts described here for the placement of the various sensor configurations described, of course.) Thus it can be seen that at one end of the tunnel 201 the opening is nearly round where in the middle it is quite oblong and again round at the other side. The tunnel or interior space designed in this manner provides some resistance to length wise slippage of the fixture along the length of the vessel it's meant to surround as well as reducing the ability of the vessel to come out through the slit. It is also believed to enhance the sensing of pressure.

Figure 21:
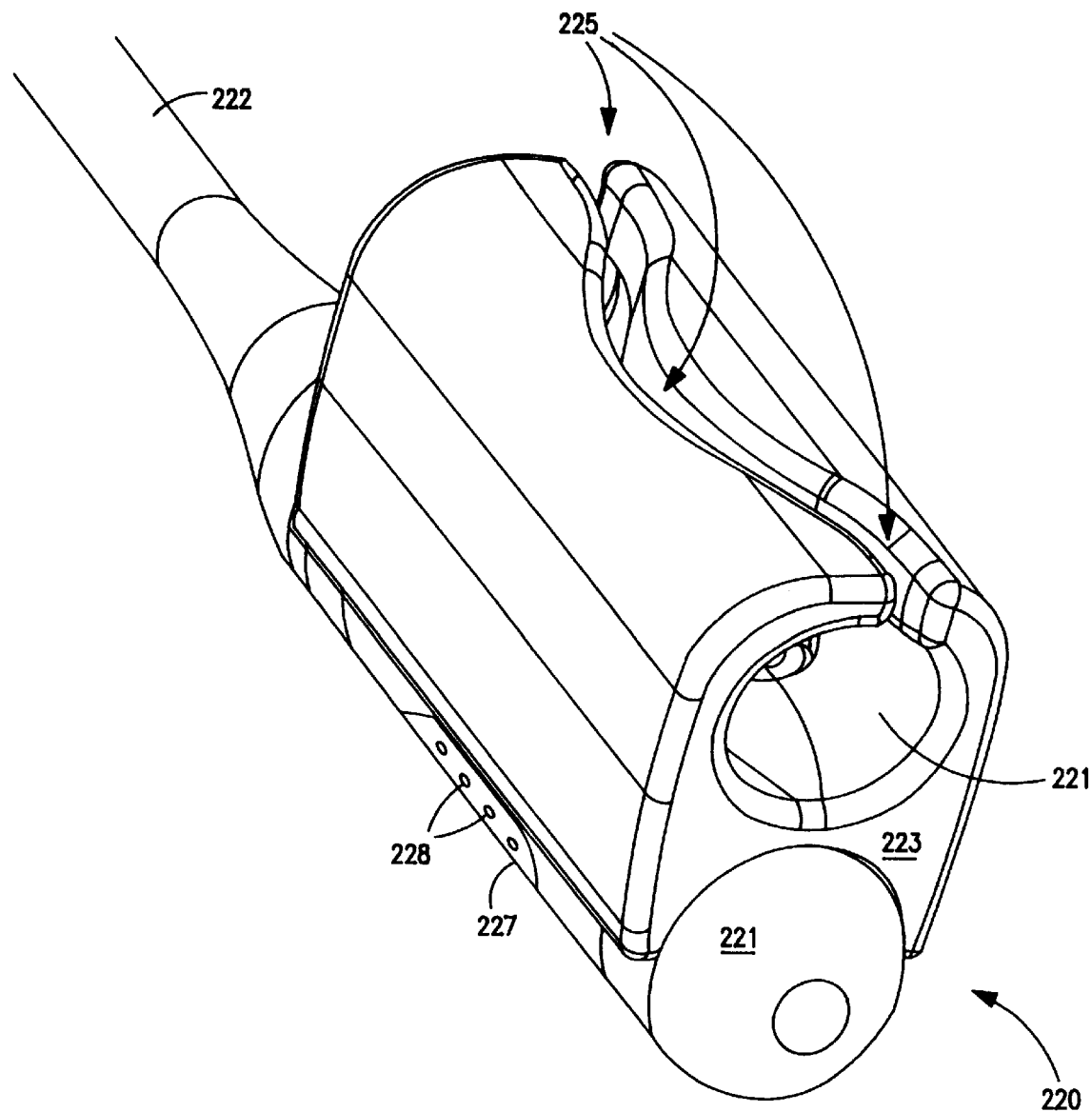
FIG. 21 is a perspective view of another preferred embodiment.

In FIG. 21, a convolved, curved or serpentine slit design is shown in slit 225 on device 220. It is certainly within the range of preferred embodiments to employ both the serpentine or curved slit design or something similar together with the design of the pinched tunnel illustrated in FIGS. 20A–E in the same device, or not, if preferred. The curve of the slit shape could be more angular than that illustrated if desired as well.

In device 220, the pressure sensor capsule body 221 is again mounted to the fixture 223 but in this design, the lead 222 is built integrity with pressure capsule 221.

Figure 22:
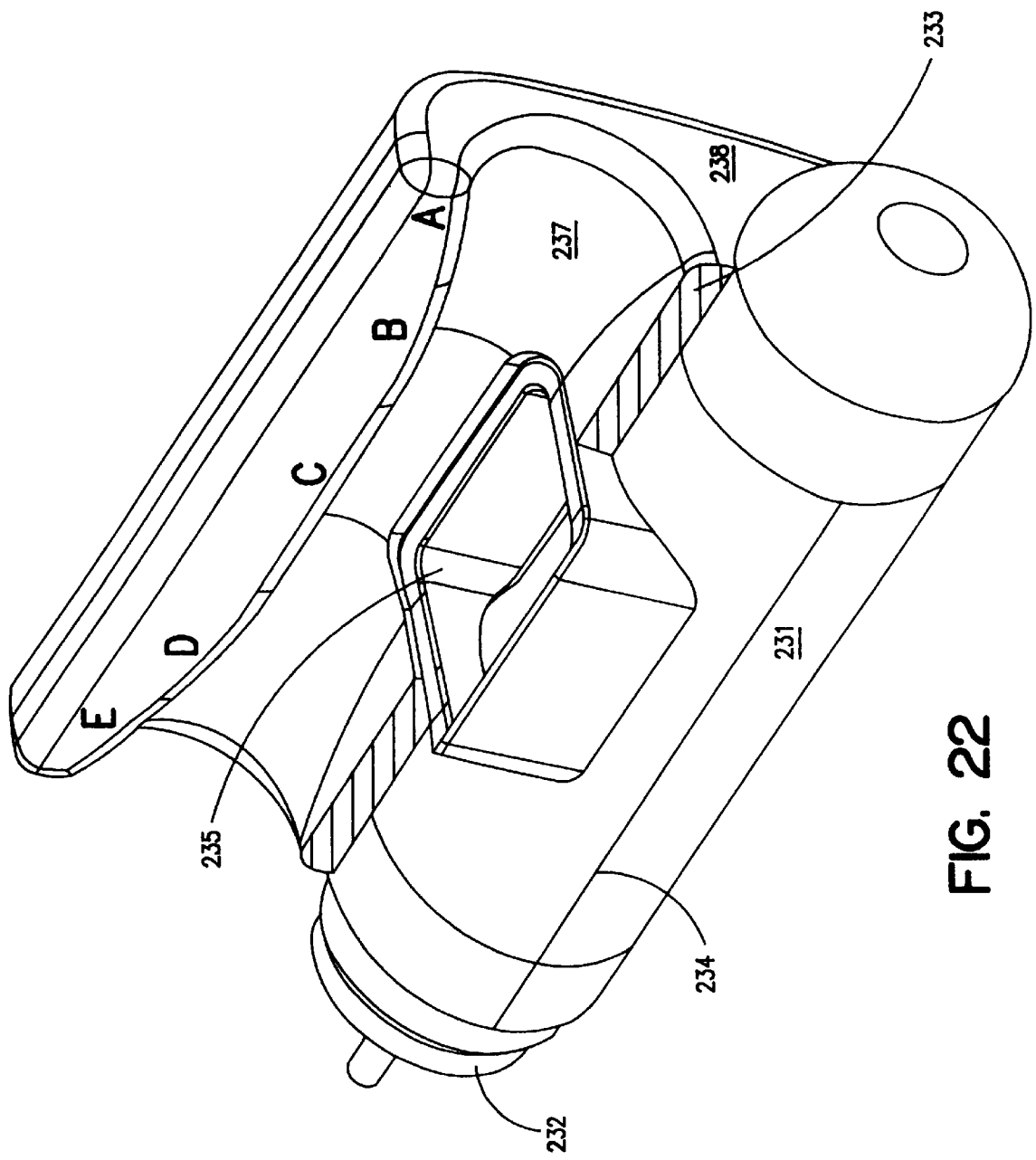
FIGS. 22 and 23 are partially sectioned perspective views of two preferred embodiments.

Refer now to FIG. 22. This holding fixture 238 and pressure capsule 231 can be designed as an integrated device or assembled in the operating room by the surgeon to form device 230. As in the device illustrated in FIG. 20, an attachment mechanisim for attaching the lead to the pressure capsule 231 is also illustrated at 232. Thus, the device can be a 2 or 3 piece combination, that is, a capsule and lead joined to a fixture, or a capsule joined to the lead and the fixture separately. In this device design, either a pressure transmissible substance 235 (preferably medical adhesive although other similar substances can be used), or an actual pressure diaphragm surface should mate smoothly with the interior surface 237 of the device 230. Surround structure or tub 234 can be formed integrally with either the sensor and or pressure capsule 231 or with the material 233 of which the fixture is made, depending on whether it is easier to manufacture with the surround 234 holding the fixture to the pressure sensor capsule 231 or to the fixture 238.

Figure 23:
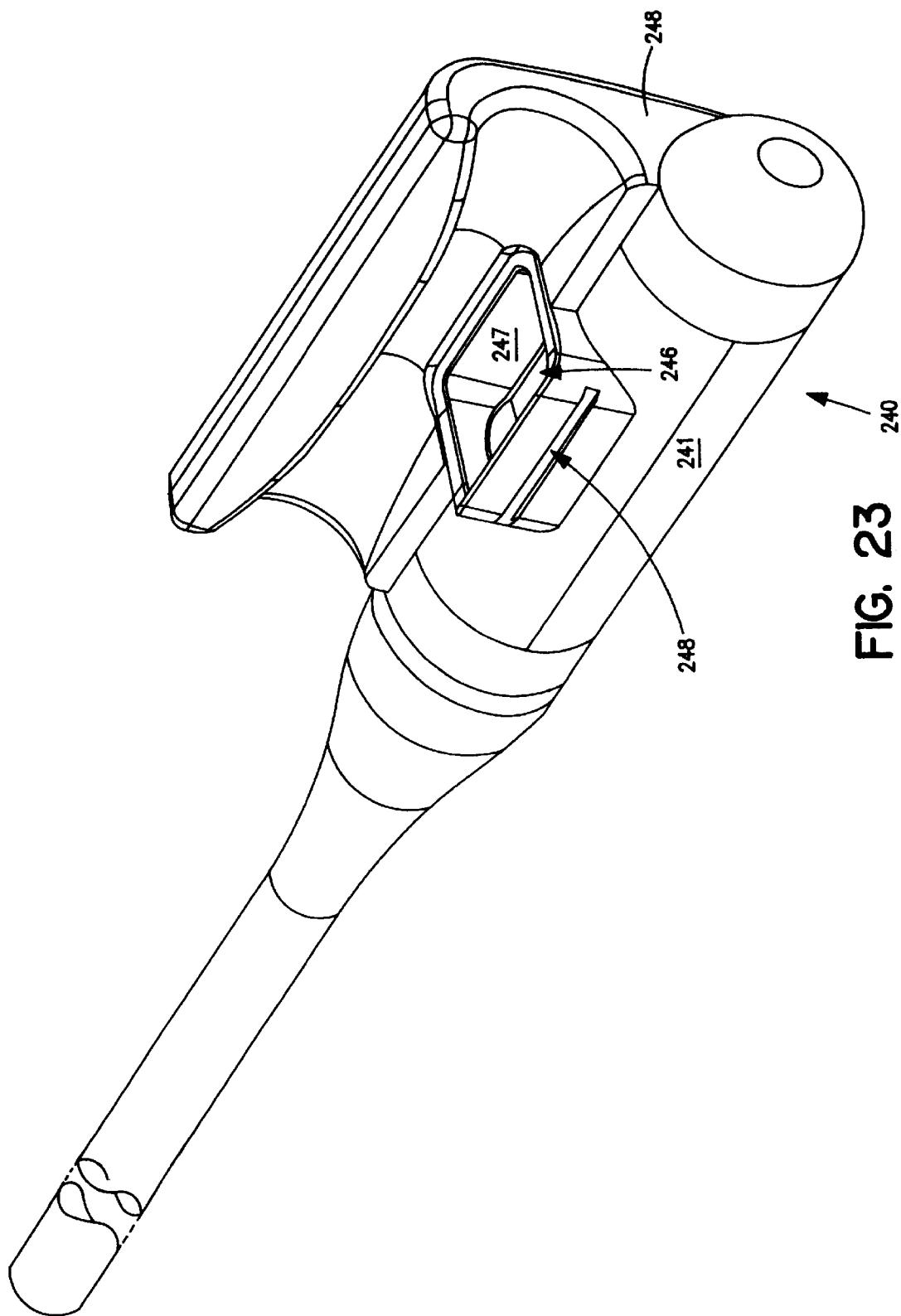

In FIG. 23 the inventive device 240 is again shown to be built of two main parts; the fixture 248 and the capsule in which the sensors are located 241. In this particular design a pressure sensor diaphragm 246 is built below the upper surface of the mating tub 247 which will be filled with pressure transmissive substance in the preferred embodiment. In this design, it can be seen that the fixture 248 can simply be snapped over the mating tub 247 to employ a ridge of the same material as fixture 248 (not shown) which will mate with the detent 248 in the mating tub 247.

Currently since it is cheaper to manufacture the fixture part, if the reader wishes to accommodate the surgeon, a kit containing a plurality or multiplicity of fixtures of different sizes which can all mate to a single sensor capsule provides a most cost effective solution.

Thus, since presently configured pressure capsules like 241 are made of a metal like titanium, for this design it would be easiest to form the mating tub 247 with its mating detents 248 on the surface of that metal capsule. To manufacture, the next step would be to fill the tub with medical adhesive or other suitable pressure transmissive medium, wait for the pressure transmissive medium to cure, sterilize the whole thing and provide it to a physician or surgeon with a set of sized fixtures like that illustrated at 248. In this way, a kit could be provided so that the right sized fixture 248 could be picked from a kit of a range of such fixtures to mate with a single sterilized and prepared pressure capsule and lead combination. Of course this would be applicable to the pressure capsule without a lead or with a lead connector as illustrated in FIG. 22 for example, and to other sensor capsules containing sensors other than pressure sensors with minor accommodation. For examples, an oxygen sensor requiring that its sensor be touching the vessel would omit the steps of providing a pressure transmissive medium, and an impedance sensor may simply provide electrical connections to the fixture which may itself have electrodes mounted strategically around the tunnel formed by the fixture to contact the vessel most appropriately.

Figure 24:
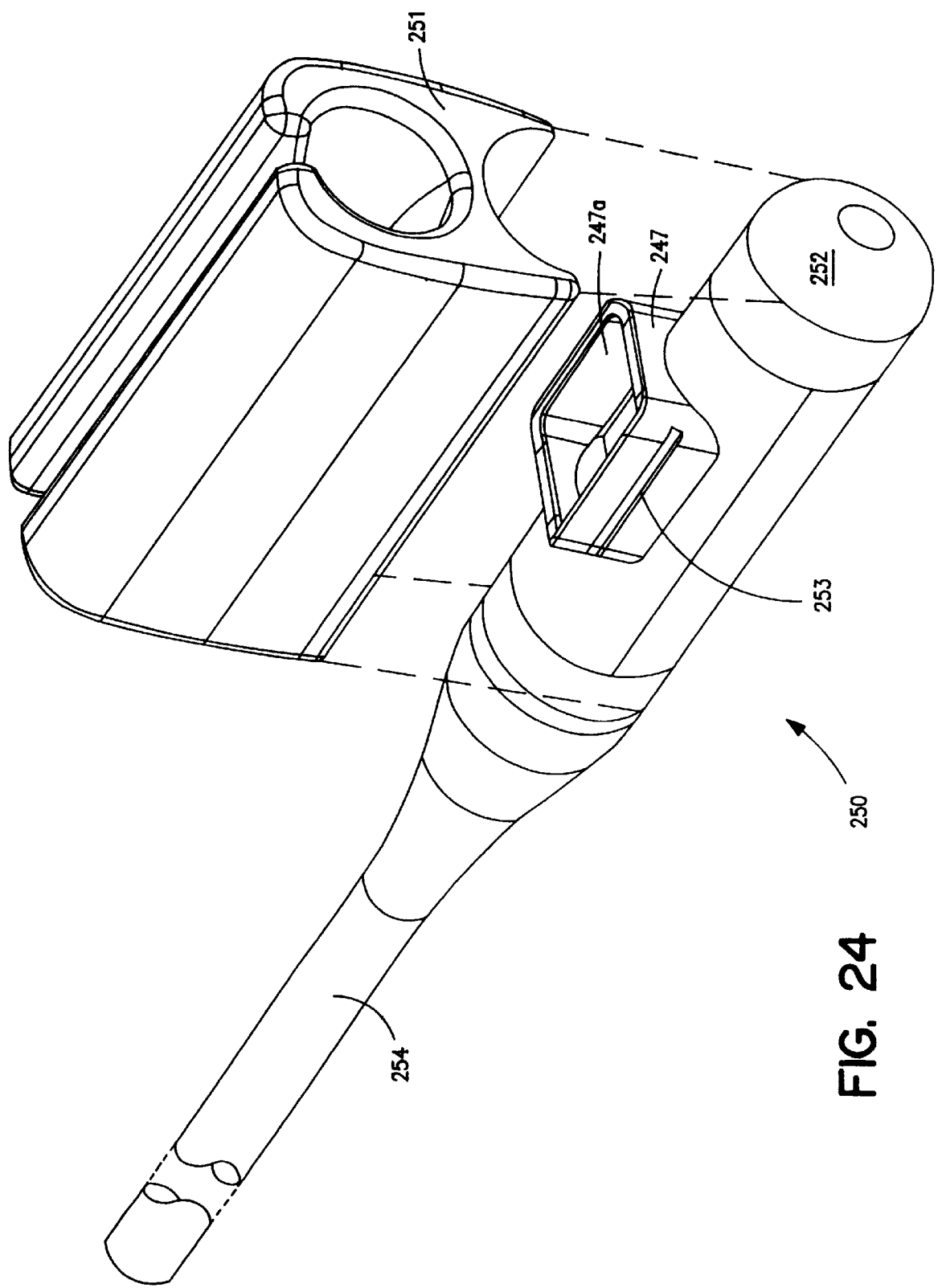
FIG. 24 is an exploded perspective view of a preferred embodiment of the invention, illustrating one manner of connecting two components in accord with the inventive concepts described herein.
Figure 25:
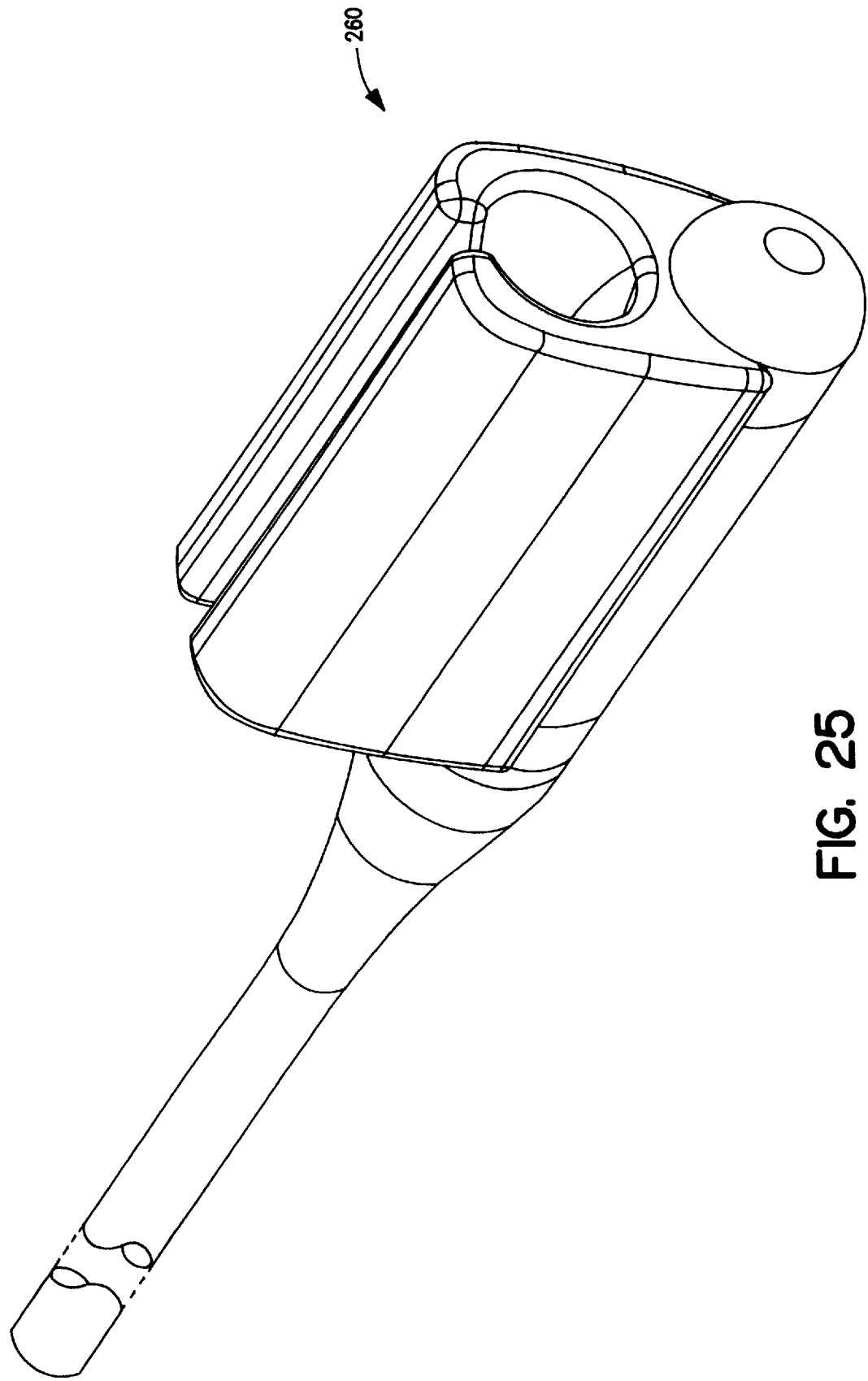
FIG. 25 is an assembled structure of the exploded view of FIG. 24.

FIG. 24 shows the combination 250 of the pressure capsule 252 having the mating tub 257 filled with pressure transmissible substance 247a which can come from one sterile package. Selecting the correctly sized fixture 251 and pressing it over the sensor package 252 will provide a reassuring snap to the physician when the internal ridges or ridge mate with the detent 253 and produce the device of FIG. 25, 260. Other mechanical links which may be well known in the art can be substituted for a ridge with mating detent. Bumps and detents, set screws and glue describe just a few of these.

While it is assumed that a certain level of background is available to the reader, it is useful to mention and thus incorporate by reference a number of patents which describe features that may be employed in implementing the mentioned features of this invention including the use of multiple implantable devices having the inventive fixtures, which can communicate with each other or with other implanted devices with or without provision of conductors (for examples of background in this area see U.S. Pat. Nos. 4,987,897 and 5,113,859 issued to Funke), telemetry uplink and data storage for monitoring and communication with an external receiver generally (U.S. Pat. Nos. 5,411,031, 5,687, 734, and 5,693,676), ultrasound transducers used in implantable devices (U.S. Pat. No. 5,188,106), and Drug pumps (U.S. Pat. Nos. 4,373,527, 5,681,285 and 5,586,629).

Figure 26:
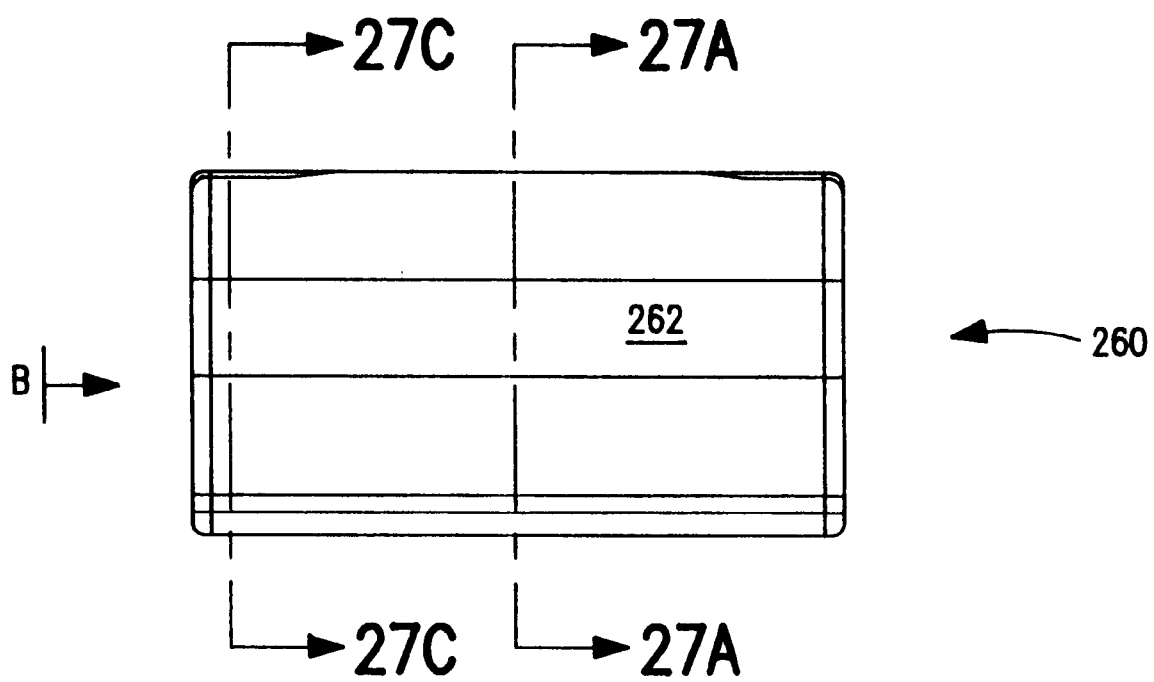
FIG. 26 is a side view of one form of the upper part of the fixture in accord with a preferred embodiment.
Figure 27A:
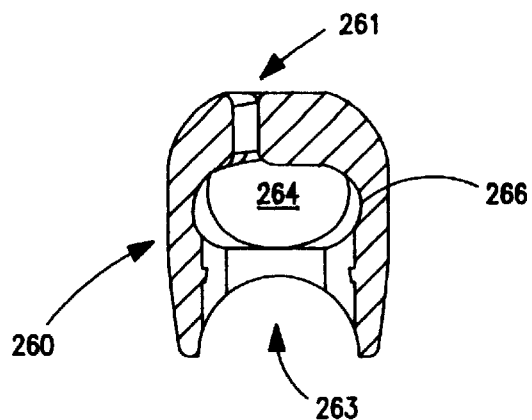
FIGS. 27A, 27B and 27C are a facing view, and two sectional views of the device of FIG. 26.
Figure 27B:
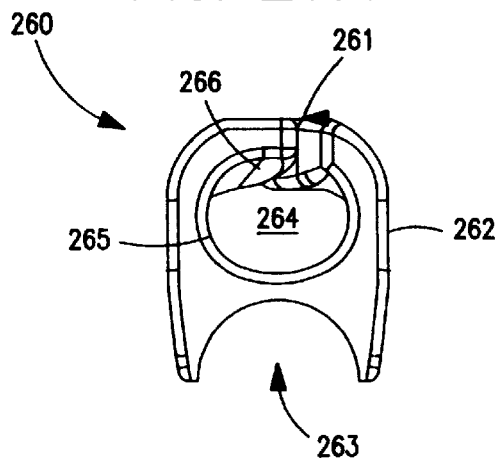
Figure 27C:
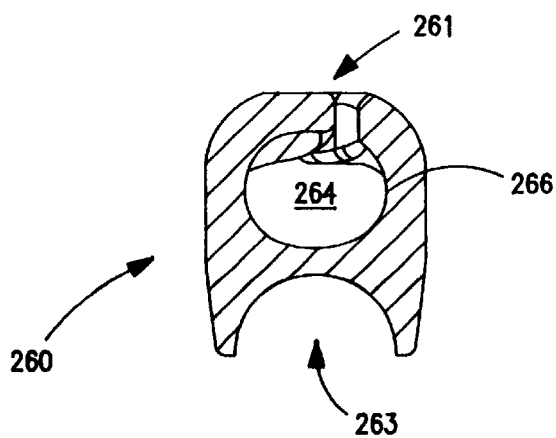

To further illustrate the use of tunnel narrowing along with a curved slit design, the illustrations of FIG. 26 and FIGS. 27A–C should be considered. FIG. 27B is a facing view looking into the tunnel 264. It should be noted that this part of the device structure when assembled will hold the pressure capsule or other sensor housing at location 263 where the fixture curves inward toward the central passageway or tunnel 264. It can be noted that the upper portion of the tunnel 266 can be seen narrowing past this entry way which is nearly round at perimeter 265 from this view. Note also that the sidewall 262 corresponds to sidewall 262 on FIG. 26.

Referring to the section taken at line CC from FIG. 26, one can see that the diameter 266 has only slightly started to become elliptical around the tunnel passage way 264. However, in FIG. 27A taken at section line AA from FIG. 26, a perimeter 265 of the tunnel can be seen as quite elliptical in shape and the curve of the slit 261 can be seen to have substantially moved in its location in FIG. 27B, the facing view taken at line B.

If desired of course, a clip similar to that illustrated in FIG. 1 may be used to further insure that no blood vessel may escape the tunnel passageway 264.

Certainly many variations on the features described herein and many cross combinations thereof may be made use of without leaving the ambit of this disclosure, which is deemed limited only as set forth in the following appended claims.

What is claimed is:

1. A kit for use during surgery to implant a medical device comprising:

a sterilizable package containing a sensor capsule, and
   a sterilizable package containing a sized fixture, said sized fixture being one of a series of sized fixtures, said fixtures comprising a tube member having an opening at both ends and a slit opening connecting both open ends, said tube member being sized in relation to body blood vessels.

2. A kit as set forth in claim 1 wherein said sensor capsule is a pressure capsule.

3. A kit for use during surgery to implant a medical device comprising:

a sterilizable package containing a sensor capsule, and
   a sterilizable package containing a plurality of sized fixtures, each said sized fixture being one of a series of sized fixtures, said fixtures comprising a tube member having an opening at both ends and a slit opening connecting both open ends, each said tube member being sized in relation to body blood vessels.

4. A kit as set forth in any of claims 1–3 wherein said sensor capsule is permanently connected to a medical lead.

5. A kit as set forth in any of claims 1–3 wherein said sensor capsule contains a connection for connecting to a medical lead.

6. A kit as set forth in claim 1 wherein said fixture slit is also sized.

7. A kit as set forth in claim 3 wherein each said fixture slit is also sized.

8. A kit as set forth in any of claims 1–3, 6, or 7 further comprising a separate clip member for sealing a vessel in said fixture.

9. An implantable medical device adapted to be configured for implant during surgery, comprising at least two portions to be assembled during surgery:

a pressure sensor capsule portion wherein a pressure sensor is mounted in a capsule that is formed for connection to a medical electrical lead having electrical conductors therein and wherein said capsule further comprises a mounting tub surrounding said pressure sensor and having a mechanical connector for connecting to another of said at least two portions, and
   a fixture portion comprising a mating mechanical connector for mating to said pressure sensor capsule mechanical connector, and a tube portion for surrounding said mounting tub such that when connected said tub presents said pressure sensor to an inside of said tube portion.

10. A method of manufacturing a implantable medical device adapted to be configured for implant during surgery, comprising at least two portions to be assembled during comprising:

building a pressure sensor capsule with a connecting tub mounted thereon, said connecting tub having a mating mechanical connector formed therein, and
   building a fixture device with a mating member for snappable mating with said tub mating mechanical connector.

11. A method for manufacturing a fixture assembly from a rectangular block of medically compatible metal comprising:

machining rounded external shape as desired, machining a substantially round passage hole lengthwise through said block, machining an opening slit on one side of said block so as to connect said passage hole along its entire length with a lengthwise surface of said block, machining out by wire electrical discharge machining an electronics bay for containing electronics opposite said lengthwise surface of said block, and machining out by wire electrical discharge machining a rectangular hole perpendicular to said passage hole, near enough to said electronics bay so as to form a flexible diaphragm between said electronics bay and said passage hole.

12. A method as set forth in claim 11, further comprising:

mating an electronics and sensor platform to a surface of said electronics bay coplanar with said diaphragm, and sealing said electronics bay into a capsule by mating said capsule with said block at a side formed by said electronics bay.

13. An implantable medical device adapted to be configured for implant during surgery, comprising at least two portions to be assembled during surgery:

a sensor capsule portion wherein a sensor means is connected by a capsule member constructed for connection to a medical electrical lead and wherein said capsule member further comprises a mounting unit having a mechanical connector for connecting to another of said at least two portions, and a fixture portion comprising a mating mechanical connector for mating to said sensor capsule mechanical connector, and a tube portion for surrounding said mounting unit such that when connected said unit provides access for said sensor to an inside of said tube portion.

14. A method for implanting a chronically implantable sensor fixture comprising:

pinching or otherwise closing off the flow of blood at a location on a vessel in a living body, allowing the blood to evacuate the vessel in a vessel portion downstream from said closed off location, urging said evacuated downstream portion into a fixture of a size to hold said blood vessel, and releasing said closed off location so as to allow the flow of blood to return to said downstream portion.

15. A method of implanting a chronically implantable sensor into a living body on a vessel of said body comprising:

selecting an appropriately sized sensor fixture for mounting around a said vessel, clipping said fixture to a sensor capsule, and mounting said fixture with said sensor capsule to said vessel.

16. A method as set forth in claim 15 further comprising:

clipping a spring clip around said fixture.

17. A method as set forth in claim 15 further comprising:

connecting a lead to said sensor capsule for providing sensor signals to another implantable medical device which may also be implanted in said living body.

* * * * *